United States Patent [19]

Miltenberger

[11] Patent Number: 5,292,928
[45] Date of Patent: Mar. 8, 1994

[54] PROCESS FOR THE REACTION OF A LOW-MOLECULAR HYDROXYL COMPOUND WITH A CARBOXYLIC ACID HALIDE

[75] Inventor: Karlheinz Miltenberger, Gersthofen, Fed. Rep. of Germany

[73] Assignee: Hoechst Aktiengesellschaft, Frankfurt am Main

[21] Appl. No.: 917,050

[22] PCT Filed: Jan. 24, 1991

[86] PCT No.: PCT/JP91/00131
§ 371 Date: Jul. 31, 1992
§ 102(e) Date: Jul. 31, 1992

[87] PCT Pub. No.: WO91/11423
PCT Pub. Date: Aug. 8, 1991

[30] Foreign Application Priority Data
Feb. 2, 1990 [DE] Fed. Rep. of Germany ....... 4003014

[51] Int. Cl.⁵ ............... C07C 69/76; C07C 69/63; C07C 53/00
[52] U.S. Cl. .................................. 560/226; 560/8; 560/100; 560/103; 560/106; 560/110; 560/111; 560/112; 560/113; 560/124; 560/227; 560/228; 560/116; 560/117; 560/119; 562/400; 562/405; 562/493; 562/497; 562/512; 562/602; 562/606
[58] Field of Search ............ 560/226, 227, 228, 8, 560/100, 103, 106, 110, 111, 112, 113, 124, 227, 228, 116, 117, 119; 562/400, 405, 493, 497, 512, 502, 606

[56] References Cited

FOREIGN PATENT DOCUMENTS 0004957 10/1979 European Pat. Off. ............ 560/228
2059131 12/1970 Fed. Rep. of Germany ...... 560/226
0707908  1/1980 U.S.S.R. ............................. 560/228

Primary Examiner—José G. Dees
Assistant Examiner—Keith MacMillan

[57] ABSTRACT

In a process for reacting a low molecular weight hydroxy compound with a carboxylic acid halide, a small amount of the acid halide is introduced into the reaction vessel and the remainder of the acid halide and the hydroxy compound are added gradually in an approximately stoichiometric ratio. The hydrogen halide formed is thus prevented from dissolving in the reaction medium. The heat of reaction to be dissipated is negligible.

8 Claims, No Drawings

PROCESS FOR THE REACTION OF A LOW-MOLECULAR HYDROXYL COMPOUND WITH A CARBOXYLIC ACID HALIDE

The invention relates to a process for the environmentally friendly reaction of a low-molecular hydroxyl compound with an aliphatic carboxylic acid halide, especially of alcohols with acid chlorides.

In the preparation of esters from acid chlorides and hydroxyl compounds, the alcohol component is conventionally introduced into the reaction vessel first and the acid chloride is metered in according to the permissible temperature and pressure relationships. HCl gas is produced in this procedure and initially dissolves in the alcohol component with the evolution of heat. HCl gas is not released until saturation has been reached. The advantage of this procedure is that an uncontrollable reaction of the acid chloride with undesired hydroxyl compounds, for example water in the event of a condenser fracture, can be excluded. The essential disadvantage of this procedure is that the HCl gas formed in the reaction is absorbed in the alcohol initially introduced, with the evolution of a substantial heat of solution, and undergoes undesired secondary reactions with the alcohol component. In the case of the preparation of methyl dichloroacetate from methanol initially introduced and dichloroacetyl chloride metered in, methyl chloride and water are formed in a temperature-dependent secondary reaction. At a temperature of only a little above 40° C., considerable amounts of methyl chloride are formed, which is undesired on account of its polluting properties. Methyl chloride can even be detected in the released HCl gas in the temperature region below 40° C., creating the need for a special purification of the effluent gas.

In the working-up of such a reaction mixture, especially in the presence of readily saponifiable esters such as e.g. methyl dichloroacetate, the water which is also formed in this secondary reaction results in an undesired saponification, i.e. in a possibly substantial reduction of the ester yield.

It has now been found that the above-described disadvantages in the preparation of esters from acid halides and low-molecular hydroxyl compounds can be avoided by a procedure in which the acid halide is initially introduced and the hydroxyl compound is metered in.

The invention thus relates to the process described in the claims.

In the process according to the invention, low-molecular hydroxyl compounds are reacted with acid halides. Suitable hydroxyl compounds are water, aliphatic $C_1$–$C_{12}$ alcohols, cycloaliphatic $C_6$–$C_{12}$ alcohols and aromatic alcohols. It is preferred to use water, aliphatic $C_1$–$C_{12}$ alcohols and cycloaliphatic $C_6$–$C_{12}$ alcohols, especially water and aliphatic $C_1$–$C_4$ alcohols, for example methanol, ethanol, n- and i-propanol and butanols.

Suitable carboxylic acid halides are the fluorides, chlorides and bromides, preferably bromides and chlorides, of aliphatic $C_2$–$C_6$ carboxylic acids, cycloaliphatic $C_6$–$C_{12}$ carboxylic acids and aromatic carboxylic acids. It is preferred to use the chlorides of lower aliphatic $C_2$–$C_6$ halogenocarboxylic acids such as, for example, chloroacetic acids or chloropropionic acids.

The reactants are reacted in such a way that the carboxylic acid halide is maintained in excess during the reaction and the hydroxyl compound is added to the acid halide. For this purpose, 5 to 20 mol % of the total amount of acid halide intended for the reaction is initially introduced into the reaction vessel and the remaining acid halide and the hydroxyl compound are then introduced gradually, in approximately stoichiometric proportions, at a rate which depends on the removal of the hydrogen halide and the heat of reaction. At the end, when the amount of acid halide to be added has been consumed, the acid halide remaining in the reaction vessel is also reacted. The hydroxyl compound is introduced into the reaction vessel in an amount of 105 to 120 mol % based on the total acid halide.

If the reactants are liquid, they are preferably brought together in undiluted form in the absence of a solvent. Solid reactants are conveniently dissolved before the reaction in an inert solvent, for example in an aliphatic, cycloaliphatic or aromatic hydrocarbon, in carbon tetrachloride or in other inert halogenated hydrocarbons, for example in trichloroethene.

The reaction temperature depends on the pressure and the reactants and is 20 to 100 and preferably 20° to 50° C. or, in the case where acid chlorides are reacted, up to 40° C. The pressure is 1 to 3 and preferably 1 to 1.5 bar.

Any apparatus suitable for esterification reactions can be used as the reaction vessel, for example flasks and kettles equipped with stirrers, reflux condenser, feed vessels and monitoring and control devices.

The reaction product formed, namely acid or ester, is obtained in pure form by generally known methods such as distillation, crystallization or some other process. In some cases, the reaction product can be used without a further purification operation.

The process according to the invention produces practically no heat of solution needing to be removed, because the hydrogen halide formed by the reaction is only slightly soluble in the acid halide. The hydrogen halide is released right from the beginning of the reaction. Acids which are not readily accessible by other methods can also be obtained by this process in good yield from their acid chlorides.

Where glass apparatuses are used, a possible fracture of the reflux condenser and penetration of cooling water into the reaction space does not cause a runaway reaction.

The following Examples will serve to illustrate the invention.

Example 1

Preparation of ethyl dichloroacetate (EDA)

500 cm$^3$ of dichloroacetyl chloride (DAC) (corresponding to 766.5 g=5.20 mol) were reacted with 319 cm$^3$ of absolute ethanol (corresponding to 251.7 g=5.46 mol) in a 2 dm$^3$ 4-necked flask equipped with an internal thermometer, a high-efficiency condenser, a stirrer, a Claisen attachment and two 500 cm$^3$ dropping funnels. To perform the reaction, 10 cm$^3$ of DAC were initially introduced into the flask, with the stirrer running, and DAC and ethanol were continuously added dropwise from both the dropping funnels, DAC being maintained in excess up to the end of the reaction. The rate of dropwise addition was regulated so that every 10 cm$^3$ of DAC reacted with 6.1 cm$^3$ of ethanol in approximately stoichiometric proportions in about 1.5 minutes. During the reaction, the mixture was cooled so as to prevent the internal temperature from exceeding 40° C. The HCl gas produced in the reaction was removed via the high-efficiency condenser.

Towards the end of the reaction, when all the DAC had been run in, the other dropping funnel still contained ca. 18-24 cm$^3$ of ethanol, which was introduced into the flask in a molar excess of 5% in order to convert the excess DAC.

During the reaction itself, the addition of DAC and ethanol had to be monitored continuously, the amount of ethanol metered in being allowed to vary only by at most ±3 cm$^3$ relative to the predetermined value. In practice, this means that, over the same periods of time, the amount of ethanol added corresponded to about 55-60% of the amount of DAC which could be read off on the dropping funnels.

When the reaction had ended, the mixture was stirred for about a further ¼ hour to complete the conversion and to remove the HCl gas. The ethyl dichloroacetate formed was then purified by vacuum distillation. 778 g of EDA were obtained after vacuum distillation, this being a yield of 95.3% based on DAC.

Example 2

Preparation of ethyl trichloroacetate (ETA)

Ethyl trichloroacetate (ETA) was also prepared in the same apparatus, analogously to the preparation of ethyl dichloroacetate.

For this purpose, 500 cm$^3$ of trichloroacetyl chloride (TAC) (corresponding to 812.5 g=4.47 mol) were reacted with 274 cm$^3$ of absolute ethanol (corresponding to 216.3 g=4.69 mol). The reaction was again carried out by a procedure in which 10 cm$^3$ of TAC were initially introduced into the reaction vessel and maintained in excess up to the end of the reaction. TAC and ethanol were continuously added dropwise from both the dropping funnels, every 10 cm$^3$ of TAC reacting with 5.2 cm$^3$ of ethanol in approximately stoichiometric proportions. The amount of ethanol metered in was allowed to vary only by at most ±2.5 cm$^3$ relative to the predetermined value.

During the reaction, the mixture was cooled and the HCl gas was removed via the high-efficiency condenser.

When all the TAC had been run in, the ethanol dropping funnel still contained ca. 16-21 cm$^3$ of ethanol, which was added in excess in order to convert the excess TAC.

When the reaction had ended, the mixture was stirred for about a further ¼ hour. The ethyl trichloroacetate was then purified by vacuum distillation.

778 g of ETA were obtained, this being a yield of 91% based on TAC.

Example 3

Preparation of n-butyl trichloroacetate (BTA)

Butyl trichloroacetate was prepared analogously to Example 1. 500 cm$^3$ TAC (812.5 g, corresponding to 4.47 mol) were reacted with 429.4 cm$^3$ of n-butanol (347.8 g, corresponding to 4.69 mol) in the apparatus described. The reaction was again carried out by a procedure in which 10 cm$^3$ of TAC were initially introduced into the reaction vessel and 10 cm$^3$ of TAC and 8.2 cm$^3$ of n-butanol were metered in over the same periods of time. The amount of butanol metered in was allowed to vary only by at most ±4 cm$^3$ relative to the predetermined value.

When the reaction had ended, the remaining n-butanol, i.e. 25-33 cm$^3$, was added, the mixture was stirred for a quarter of an hour and the ester formed was distilled under vacuum. The yield was 915 g of BTA, i.e. 93.3% based on TAC.

Example 4

Preparation of methyl dichloroacetate (MDA)

2590 dm$^3$ of DAC (corresponding to 4000 kg=27.14 kmol) were reacted with 1150 dm$^3$ of methanol (corresponding to 910 kg=28.4 kmol) in a 4 m$^3$ stirred kettle.

For this purpose, 30 dm$^3$ of DAC were initially introduced into the stirred kettle, with the stirrer running, and methanol and DAC were then metered in, in stoichiometric proportions, by means of two metering pumps driven by one motor via a common drive shaft.

The reactants were introduced via meters and rotameters. The metering operation was carried out in such a way that 17 dm$^3$ of methanol were metered in over the same period of time in which 40 dm$^3$ of DAC were injected. These amounts were set at the metering pumps and continuously monitored. The amount of methanol metered in was allowed to vary only by at most ±8 dm$^3$ relative to the predetermined aggregate desired value. In this process, the methanol reacted with the DAC to give MDA with a slightly exothermic heat tonality. The heat of reaction was removed by means of jacket cooling. The temperature did not exceed 40° C.

As ca. 30 dm$^3$ of DAC were present in excess in the reactor throughout the entire reaction, there was a vigorous production of HCl gas right from the start. In the present case, the stirred kettle was provided with a column and attached glass condensers through which the HCl gas was released. Any entrained product was retained in the condensers and dripped back into the reaction vessel. For safety reasons, the unit was operated in such a way that the pressure of HCl gas in the unit did not exceed 1.2 bar. After about 7.5 hours, the total amount of DAC of 2590 dm$^3$ (including the 30 dm$^3$ initially introduced) DAC [sic] had reacted with 1100 dm$^3$ of methanol. This point was signalled by a cessation of HCl production and a drop in the pressure in the unit. To complete the reaction, a further 50 dm$^3$ of methanol were then metered in and the whole mixture was stirred for 15 minutes.

The reaction mixture was subsequently distilled under vacuum to give 3650 kg of MDA, this being a yield of 94.3% based on DAC.

Example 5

Preparation of dichloroacetic acid (DAA)

Analogously to the preparation of MDA, 2590 dm$^3$ of DAC (corresponding to 4000 kg=27.14 kmol) were reacted with 540 dm$^3$ of water (540 kg=30 kmol) in the same 4 m$^3$ stirred kettle.

For this purpose, 30 dm$^3$ of DAC were again introduced initially into the stirred kettle. The remaining DAC was then metered in with the water in stoichiometric proportions.

The reactants were introduced analogously via meters and rotameters. The metering operation was carried out in such a way that 7.5 dm$^3$ of water were injected over the same period of time in which 40 dm$^3$ of DAC were metered in. The amount of water metered in was allowed to vary by at most ±3 dm$^3$ relative to the predetermined aggregate desired value; it was continuously checked. The DAC excess of 30 dm$^3$ was maintained up to the end of the reaction. After ca. 7 hours, the total amount of DAC of 2510 dm$^3$ (including the 30 dm$^3$ initially introduced) had reacted with 490 dm$^3$ of water. To complete the reaction, a further 50 dm$^3$ of water were then metered in and the mixture was stirred for 15 minutes. Subsequent vacuum distillation gave 3390 kg of dichloroacetic acid, this being a yield of 96.8% based on DAC.

What is claimed is:

1. A process for the preparation of a carboxylic acid or carboxylic acid ester by reacting, in a reaction zone, a hydroxyl compound and a carboxylic acid halide, comprising the steps of:

introducing into the reaction zone 5 to 20 mol % of the total amount of carboxylic acid halide to be reacted, introducing into the reaction zone over a period of time the remainder of said total amount of carboxylic acid halide while introducing into the reaction zone a first amount of hydroxyl compound, said first amount of hydroxyl compound being approximately stoichiometric with respect to said remainder, the rate of introduction of said first amount of hydroxyl compound being approximately stoichiometric with respect to the rate of introduction of said remainder, so that during and at the conclusion of the introduction of said first amount of hydroxyl compound, essentially unreacted carboxylic acid halide is present in the reaction zone, adding a second amount of hydroxyl compound which is at least stoichiometric with respect to said essentially unreacted carboxylic acid halide present in the reaction zone at the conclusion of the introduction of said first amount of hydroxyl compound, the total of said first amount and said second amount of hydroxyl compound being 105 to 120 mol %, based on said total amount of carboxylic acid to be reacted.

2. A process as claimed in claim 1, wherein the hydroxyl compound comprises water, in which case the product formed in the reaction zone comprises a carboxylic acid, or a C$_1$–C$_{12}$–alcohol, in which case the product formed in the reaction zone comprises a carboxylic acid ester.

3. A process as claimed in claim 2, wherein the hydroxyl compound comprises water, and a carboxylic acid is recovered from the reaction zone as the product of the process.

4. A process as claimed in claim 2, wherein the hydroxyl compound comprises an aliphatic C$_1$–C$_{12}$–alcohol, and a carboxylic acid ester is recovered from the reaction zone as the product of the process.

5. A process as claimed in claim 1, wherein the hydrogen halide formed as a byproduct of the reaction of the carboxylic acid halide and the hydroxyl compound is released from the reaction zone at the beginning and during said reaction, due to the low solubility of the hydrogen halide in carboxylic acid halide.

6. A process as claimed in claim 1, wherein the carboxylic acid halide is a chloride of an aliphatic C$_2$–C$_6$–halogenocarboxylic acid.

7. A process as claimed in claim 1, wherein the carboxylic acid halide and the hydroxyl compound are both liquids and are reacted in the reaction zone essentially in the absence of a solvent.

8. A process for the preparation of a halogenocarboxylic acid or a halogenocarboxylic acid ester by reacting, in a reaction zone, halogenocarboxylic acid chloride with water or a C$_1$–C$_{12}$-alcohol, comprising the steps of:

first introducing into the reaction zone 5 to 20 mol % of the total amount of halogenocarboxylic acid halide to be reacted, then metering into the reaction zone over a period of time the remainder of said total amount of halogenocarboxylic acid halide, while, over essentially the same period of time, metering into the reaction zone a first amount of water or said alcohol, said first amount of water or said alcohol being approximately stoichiometric with respect to said remainder, the rate of metering of said first amount of water or said alcohol being substantially the same, on a molar basis, as the rate of metering of said remainder, so that during and at the conclusion of the metering-in of said first amount of water or said alcohol, at least about 5 mol % of essentially unreacted halogenocarboxylic acid halide, with respect to said total amount of carboxylic acid halide to be reacted, remain in the reaction zone, throughout this metering step, removing hydrogen chloride from the reaction zone, adding a second amount of water or said alcohol which is in excess over stoichiometry with respect to said essentially unreacted halogenocarboxylic acid halide remaining in the reaction zone, the total of said first amount and said second amount of water or said alcohol being 105 to 120 mol %, based on said total amount of halogenocarboxylic acid, and recovering the resulting halogenocarboxylic acid or halogenocarboxylic acid ester from the reaction zone as the product of the process.

* * * * *